United States Patent [19]

Batz et al.

[11] Patent Number: 4,742,159

[45] Date of Patent: May 3, 1988

[54] DIGITALIS ANTIBODIES, PROCESS FOR THE PREPARATION THEREOF AND THE USE THEREOF FOR THE THERAPY OF DIGITALIS INTOXICATIONS

[75] Inventors: Hans-Georg Batz; Herbert Jungfer; Helmut Lenz, all of Tutzing; Albert Röder, Seeshaupt, all of Fed. Rep. of Germany

[73] Assignee: Boehringer Mannheim GmbH, Mannheim, Fed. Rep. of Germany

[21] Appl. No.: 563,217

[22] Filed: Dec. 19, 1983

[30] Foreign Application Priority Data

Nov. 26, 1983 [DE] Fed. Rep. of Germany ....... 3342870

[51] Int. Cl.⁴ .................... C07K 13/00; C12Q 1/00; C12P 21/00
[52] U.S. Cl. .................................... 530/388; 530/387; 530/389; 530/391; 530/413; 530/415; 530/416; 424/85; 514/6; 435/7; 435/68; 435/69; 436/538; 436/541
[58] Field of Search ............... 424/85, 88; 260/112 B, 260/112 R; 436/538, 541; 210/656; 435/7, 188, 68, 69; 514/6, 2; 530/387, 388, 389, 391, 413, 415, 416

[56] References Cited

U.S. PATENT DOCUMENTS 3,790,475  2/1974  Eaton ................................ 210/316
4,081,245  3/1978  Polito ............................... 23/230.6
4,081,246  3/1978  Polito ............................... 23/230.6

OTHER PUBLICATIONS

Sugura et al, *Chemical Abstracts*, vol. 94, No. 135598n, "New Immunochemical Conjuguko", 1981, p. 396.
Iskikaur et al, *Chemical Abstract*, vol. 89, No. 19774g, 1978, "Antigen and Antibody Determinator", p. 301.
Smith et al, *New England J. Med.*, vol. 307, No. 22, pp. 1357-1362, Nov. 1982, "Treatment of Life-Threatening Digitalis Intoxication . . . ".
Smith et al, *New England J. Med.*, vol. 294, No. 15, 1976, pp. 797-800, "Reversal of Advanced Intoxication with Fab Fragments of Digoxin-Specific Antibodies".

*Primary Examiner*—Thomas G. Wiseman
*Assistant Examiner*—Robin L. Teskin
*Attorney, Agent, or Firm*—Felfe & Lynch

[57] ABSTRACT

The present invention provides a process for the preparation of digitalis antibodies in which appropriate mammals are immunized with a digoxin bound to protein, the animal serum is obtained, the immune globulin-containing protein fraction is separated in known manner, the immunologically-active globulins are adsorbed on an immunologically-active column and separated from the other proteins, the antibodies are again eluted from the column and the Fab fractions are split with papain and purified, wherein, as immunologically-active adsorbent, there is used an inorganic matrix of large surface area to which digitoxin aldehyde is bound via a spacer which cannot be split with papain and the splitting off of the Fab fraction from the antibodies is carried out on the matrix.

The present invention also provides digitalis antibodies obtained by this process, which antibodies can be used for the therapy of digitalis intoxications and for preparing immunological reagents for the determination of digitalis glycosides.

9 Claims, No Drawings

DIGITALIS ANTIBODIES, PROCESS FOR THE PREPARATION THEREOF AND THE USE THEREOF FOR THE THERAPY OF DIGITALIS INTOXICATIONS

The present invention is concerned with digitalis antibodies, which can be used for the therapy of digitalis intoxications, and with the preparation of such digitalis antibodies.

Hitherto, the therapy of digitalis intoxications has been a problem. In the foreground, there was the treatment of the symptoms, especially of the life-threatening disturbances of the heart rhythm, and a forced elimination of glycosides. These measures required several days treatment under intensive care. Nevertheless, the degree of mortality is high: about 20% of the patients die of uncontrollable disturbances of the heart rhythm. In practice, very severe poisonings can occur if the preparations are taken in too high a dosage due to carelessness or as a result of an attempt at suicide or due to kidney failure so that the active material is not eliminated for several days and thereby accumulates in a toxic amount.

Therefore, there is a need for an agent which neutralises the toxic action of glycosides in the body and eliminates these quickly and effectively from the body.

This task is solved by the digitalis antibodies provided by the present invention, which are outstandingly suitable as antagonists not only for digoxin but also for digitoxin and a number of other heart glycosides.

As long ago as the early 1960's, digoxin antibodies were used in radio-immunoassays for the determination of digoxin (cf. Federal Republic of Germany patent specification No. 23 31 922).

J. Curt et al. later published a method of isolation for sheep anti-digoxin-Fab fragments (hereinafter called Fab) for therapeutic use in humans (Proc. Nat. Acad. Sci. USA, 68, 2401/1971). Sheep are thereby immunised with digoxin bound to albumin, the serum is obtained and the gamma globulin fraction is precipitated out with ammonium sulphate by known methods. The globulins are split with papain in homogeneous solution and the specific glycoside-binding Fab fragments are adsorbed with an ouabain-cellulose matrix and subsequently again eluted with ouabain. The ouabain-Fab complex is dissociated by denaturing the protein with guanidine hydrochloride and ouabain and guanidine are separated off by dialysis. The Fab protein denatured by the guanidine treatment is again renatured by dialysis against physiological buffer solution. For an economic preparation of digoxin antibodies, this process suffers from several disadvantages:

1. By the binding to ouabain, those antibodies are preferably isolated which display a strong cross-reaction with ouabain and antibodies which are specific for digoxin and, therefore, do not react with ouabain are discarded.

2. In the case of the dissociation of the ouabain-Fab complex, the protein component is denatured, which also results automatically in irreversible changes of the proteins. Furthermore, the dialysis requires very large volumes, a long time and careful control in order, on the one hand, completely to remove the guanidine hydrochloride and, on the other hand, to bring about a renaturing which is as extensive as possible.

3. As immune adsorbent, this process makes use of ouabain which is coupled to cellulose via ribonuclease. As a natural organic material, cellulose is practically always contaminated with bacteria so that a low-bacteria and pyrogen-free working, especially on a large scale and in the case of repeated use of the adsorbent, is not possible.

Thus, there is the further problem of finding an effective process for the preparation of an antibody with a low bacteria and pyrogen content which is specific for digoxin and digitoxin.

This problem is solved in that the gamma globulin fraction obtained in the above-described manner is adsorbed on to an adsorbent specific for digoxin antibodies, which consists of an inorganic carrier to which digitoxin is covalently bound, and the portions not binding with the digitoxin are washed out with an appropriate buffer. In a second step, the adsorbent loaded with digoxin-specific IgG is treated with papain and the Fab part of the antibody is split off from the Fc part. Papain and liberated Fc parts can be eluted and subsequently the digoxin-specific Fab fragments can be dissolved from the column with a comparatively strong elution agent and recovered.

Thus, according to the present invention, there is provided a process for the preparation of digitalis antibodies in which appropriate mammals are immunised with a digoxin bound to protein, the animal serum is obtained, the immune globulin-containing protein fraction is separated in known manner, the immunologically-active globulins are adsorbed on an immunologically-active column and separated from the other proteins, the antibodies are again eluted from the column and the Fab fractions are split with papain and purified, wherein, as immunologically-active adsorbent, there is used an inorganic matrix of large surface area to which digitoxin aldehyde is bound via a spacer which cannot be split with papain and the splitting off of the Fab fraction from the antibodies is carried out on the matrix.

The Fab fragments obtained by the process according to the present invention can be further purified in known manner by gel permeation chromatography, ion exchange chromatography or fractional precipitation, as well as by ultrafiltration, in order also to remove the last traces of disturbing impurities.

As inorganic carrier matrix there is preferably used a porous glass of appropriate pore size but other inorganic carriers with sufficiently high surface area and corresponding properties, such as silica gel, aluminium oxide gel and the like can also be used. In order to prepare the surface of the carrier for the binding of the digitoxin, the glass is treated, for example, with a spacer, such as a trialkoxysilylpropylamine or some other compound which produces free amino groups or other groups which react with digitoxin. The carrier so obtained is reacted with digitoxin which has been oxidised in known manner with periodate to give the so-called "digitoxin dialdehyde" (for this oxidation cf. Sardo et al., Chem. Pharm. Bull., 18, 94–99/1970) and the Schiff base thus obtained is reduced.

The so obtained adsorbent has the following important advantages in comparison with that disclosed by Curt et al. (see above):

1. Due to the use of an inorganic carrier, these adsorbents are practically inert towards bacterial attack and are mechanically very stable so that they can be used repeatedly.

2. Since the digitoxin is co-valently bound to the glass by a bridge which is not split by papain, the fragmentation of the antibody can take place directly on the adsorbent. It is thereby possible to wash out from the column in a gentle manner not only the foreign protein but also the Fc parts arising from the papain splitting, as well as the papain itself and thereby to separate from the adsorbed Fab antibodies. Due to this fragmentation, on the other hand, the binding ability of the adsorbent for the remaining Fab fragments is so weakened that these can again be dissolved out of the column with an appropriate desorption agent, without denaturing taking place.

3. Due to the use of digitoxin-containing adsorbents, those antibodies are especially firmly held which are specific for digitoxin, digoxin and their derivatives so that, in this manner, Fab antibodies are finally obtained which are especially effective as antagonists for the previously mentioned glycosides. The adsorption of the digoxin antibodies from the IgG-containing serum on the digitoxin-containing adsorbents takes place in a neutral to weakly acidic (pH 6–7.5) aqueous buffer and salt solutions which are usual for such separations. Neutral phosphate buffer in concentrations of from 0.01 to 0.5 M, sodium chloride and ammonium sulfate as salts in concentrations of from 0.01 to 0.5 M and especially of from 0.025 to 0.05 M are preferably used. In addition, the solution can also contain 0.01 to 0.1% by weight of a conventional wetting agent. After the papain splitting, the Fc components, as well as the papain, can be washed out of the column with these solutions.

More strongly acidic buffers of high concentration lead to a dissolving off of the antibodies or Fab fragments but also, at the same time, to a partial denaturing. Therefore, the dissolving off of the Fab fragments is preferably carried out with dilute mineral acids and especially with hydrochloric acid in concentrations of from 1 to 10 mM. Concentrations of from 2 to 5 mM are preferred since they combine a rapid dissolving off with a minimal denaturing of the Fab antibodies and can easily be separated therefrom by dialysis.

The following Example is given for the purpose of illustrating the present invention:

Example

1. Preparation of sheep anti-digoxin serum

Immunogen

Digoxin-glutaryl-O-hydroxysuccinimide is reacted in aqueous solution with protein, preferably bovine albumin or edestine (a protein from hemp seed). After separating off excess digoxin derivative, several digoxin molecules are coupled per molecule of protein on the terminal digitoxose via a glutaryl chain on to the protein.

Immunisation

About 0.5 mg. digoxin immunogen is administered intradermally in complete Freund's adjuvant to healthy sheep of at least 45 kg. body weight. At intervals of 2 and later of 4 weeks, the immunogen is again injected intramuscularly and subcutaneously in the same preparation for increasing the immune response. After 2 to 4 months, the titer in the serum of the animals reaches 1 mg. of digoxin-specific IgG/ml.

Serum collection, analysis and pool formation

Healthy animals which, in a sample collection, have reached the said titer can be used weekly for at least a year for the removal of blood from the neck vein. In random samples of the collection, the titer is continuously monitored with a radioimmune test or an enzyme immune test. Binding constants are also determined in the random samples by Scatchard-plot evaluation of the binding of radioactively-marked digoxin by definite dilutions of the antiserum samples. There is obtained, in agreement with the literature, values of $5 \times 10^9$ to $5 \times 10^{10}$ (liter/mol). In order to keep batch variations of the antiserum to be used for the Fab isolation as small as possible, blends of 20 to 50 liters of individual collections from several sheep are made up over a comparatively long period of time.

2. Preparation of the immune adsorbent

Amine group-containing glass 940 g. Controlled pore glass (Electro Nucleonics Inc., Fairfield, USA) are treated in aqueous suspension with ultrasonic waves for the removal of small particles and impurities and then heated for 3 hours with 65% nitric acid at 80° to 90° C. After washing out the acid, the glass is dried at 150° C. The purified glass is slowly stirred for about 20 hours at 85° C., under a reflux condenser, in 2.7 liters anhydrous dimethyl sulfoxide with 300 ml. 3-(triethoxysilyl)-propylamine. Excess silylamine is washed out with isopropanol and the aminated glass is again dried (60° C., weak vacuum). Yield about 1.8 liters aminopropyl glass (750 g.).

Oxidation of digitoxin 6 g. Digitoxin are reacted at ambient temperature for 20 hours in 450 ml. of a 2:1 ethanol/water mixture with the stoichiometrically equal amount of sodium periodate (1.7 g.). Insoluble precipitate is filtered off and discarded. The supernatant is evaporated to dryness on a rotary evaporator. The residue is washed twice with 100 ml. amounts of water and then dried in a vacuum over anhydrous calcium chloride. Yield 4 to 5 g. of oxidised digitoxin.

Digitoxin-glass adsorbent 4.5 g. of oxidised digitoxin are dissolved in 2.25 liters of a 2:1 ethanol/water mixture, mixed with 750 g. of aminopropyl-glass and reacted for 20 hours at ambient temperature, while slowly stirring. The glass is separated off by filtration. In the running through, digitoxin is determined by extinction measurement in UV (260 nm) and from this there is calculated the amount of fixed digitoxin. (theoretical value: 3 mg. digoxin/ml. glass volume). 4 g. Sodium borohydride are dissolved in 1 liter of double distilled water, diluted with 2 liters of ethanol and applied to the digitoxin-derivatised glass. With shaking several times, over the course of 2 hours at ambient temperature, the pH is adjusted to 7.0 to 7.4 by additions of 2N hydrochloric acid. The digitoxin initially fixed to the glass via labile Schiffs base binding is converted into a stable fixing. The digitoxin-glass immune adsorbent is thoroughly washed with ethanol/water/ethanol and then dried in a weak vacuum. Yield about 1.8 liters of immune adsorbent.

Preparation of the immune adsorbent for immediate use

The adsorbent is slurried with buffer A (50 mM phosphate pH 7.0/0.15 M sodium chloride/0.1% sodium azide), placed into a glass column provided with a frit and washed with a solution of 0.5 M sodium chloride/0.05% Tween 20, then with double distilled water and thereafter with 1 M propionic acid. Finally, it is equilibrated with buffer A. Immune adsorbent which has been used for Fab purification can be regenerated by washing with 1 M propionic acid and stored at 4° C. in buffer A. The adsorbent can be used several times without impairment of its properties. The fresh adsorbent is pre-washed immediately before use.

3. Production process for sheep anti-digoxin-Fab

The solutions used for the purification are sterilised in autoclaves or by membrane filtration. The water used for the preparation of the solutions is freed from pyrogens by distillation. Vessels and apparatus, as well as other adjuvants (for example chromatographic materials) are, depending upon their compatibility, rendered pyrogen-free by heating or by treatment with 0.5 M sodium hydroxide solution.

Preliminary purification of sheep anti-digoxin serum

For the removal of lipoproteins, 30 liters of antiserum are stirred with 300 g. "Aerosil" for 1 hour at ambient temperature. After separating off the "Aerosil" by centrifuging, the gamma globulins are precipitated from the supernatant, cooled to 4° C., by the addition of solid ammonium sulphate up to a concentration of 1.8 M. The precipitate is collected by centrifuging, dissolved in a solution of 0.15 M sodium chloride/0.1% azide and dialysed against a buffer (15 mM phosphate pH 7.1/50 mmol sodium chloride/0.002% hibitane) at 4° C. The dialysate is applied to a column of diethylaminocellulose (De 52-Cellulose, Whatman, Maidstone, England) with an exchanger volume of 16.2 liters and eluted with buffer of the same composition as the dialysis buffer. The protein running off from the column with this buffer is the IgG fraction from the sheep anti-digoxin serum serving for the Fab preparation. Protein yield about 500 to 700 g. Content of the digoxin-specific antibodies about 85 to 90% of the initial titer in the antiserum.

Specific adsorption

About 250 g. IgG fraction in about 10 liters of solution with a content of digoxin-specific IgG of 15 g. is brought to a buffer concentration of 50 mM phosphate/0.15 M sodium chloride/0.002% hibitane (pH 7.0) (buffer B). This solution is pumped at ambient temperature in the course of about 2 hours through a column filled with 2.4 liters of digitoxin-glass immune adsorbent. The specific IgG components bind to an extent of up to 90% on to the adsorbent. The adsorbent is washed with buffer B, to which has been added 0.35 M sodium chloride and 0.05% Tween 20, then equilibrated with a buffer C (75 mM phosphate pH 7.0/0.15 M sodium chloride/2 mM ethylenediamine-tetraacetic acid/10 mM cysteine/0.01% hibitane), which is suitable for the subsequent papain splitting.

Enzymatic fragmentation

The adsorbent loaded with digoxin-specific IgG is, without delay, transferred from the column into a glass vessel and mixed with 240 mg. papain dissolved in 2 liters of buffer C. Incubation is carried out for 4 hours and 15 minutes at 37° C. while slowly stirring with a metal winged stirrer. By measurement of samples of the supernatant of the adsorbent suspension in a UV photometer (280 nm) at different points of time during the incubation, the kinetics of the liberation of Fc protein and thus of the Fab formation can be monitored. At the end of the incubation, the adsorbent is again placed into a column and washed with buffer B. For the saturation of free SH groups from the papain splitting in the presence of cysteine, the adsorbent is rinsed with buffer (75 mM phosphate pH 7.5/0.15 M sodium chloride/0.01% hibitane), to which 10 mM iodoacetamide have been added. The iodoacetamide buffer remains in contact with the adsorbent for 2 hours at ambient temperature. It is then washed out with a solution of 0.15 M sodium chloride/0.01% hibitane to remove excess iodoacetamide and the adsorbent is prepared for elution with 30 mM sodium chloride solution.

Elution (ambient temperature)

For the elution of specific Fab, 3 mM aqueous hydrochloric acid is pumped through the adsorption column. The Fab protein is, in running through the column, investigated by measurement of the UV absorption (280 nm) and collected. 5 to 7 liters, containing about 11 g. of protein, are concentrated by ultrafiltration to about 200 to 250 ml. and then immediately lyophilised.

Gel permeation chromatography (4° C.)

A column of 1 meter length is filled with 7.5 liters Sephacryl S 200 (Pharmacia, Sweden) and equilibrated with buffer (5 mM phosphate pH 7.0/0.5 M sodium chloride/0.002% hibitane). About 5 g. Fab lyophilisate are dissolved in 110 ml. of equilibration buffer and chromatographed over the gel column. By recording of the UV absorption in the eluate, the Fab peak with a molecular weight of 50,000 is ascertained and collected. Yield is about 3.75 g. of gel chromatographically uniform protein. Residues of IgG, higher molecular Fab aggregates and smaller fragments are separated off. The Fab solution of about 700 to 800 ml. is concentrated by ultrafiltration to about 150 ml. and then dialysed against buffer (15 mM phosphate pH 7.5/0.15 M sodium chloride).

The chromatography is repeated for the second part of the Fab lyophilisate on the same column. Both chromatographed portions are again combined for the further steps, the first portion having been deep frozen and kept at −20° C. for intermediate storage.

Passage through DEAE-ion exchanger (4° C.)

400 ml. De 52-Cellulose (pre-treated with 0.5 N hydrochloric acid and 0.5 M aqueous sodium hydroxide solution for sterilising and freeing from pyrogens) are placed into a column and equilibrated with 10 mM phosphate buffer. Fab protein from the preceding step is adjusted by ultrafiltration to a protein concentration of about 50 mg./ml. and then the protein solution is passed through the De 52-cellulose column. The Fab protein runs through almost without delay and traces of foreign protein (for example albumin, Fc and the like) are retained. The Fab protein in the run-off is collected, if necessary concentrated by ultrafiltration to about 15 to 20 mg. protein/ml., the pH value adjusted on the electrode to 7.0 to 7.1 and sterilised by filtration through a 0.2μ membrane filter. Yield of the step 95%. End yield 5 to 6 g. of sheep anti-digoxin-Fab.

The end product is sterilised by filtration to a low bacterial count, placed into glass vessels, deep frozen and stored at −20° C.

We claim:

1. In a process for the preparation of Fab fragments of digitalis antibodies in which appropriate mammals are immunised with an agent for immunizing comprising a digoxin bound to protein, the animal serum obtained, the immune globulin-containing protein fraction is separated in known manner, the immunologically-active globulins adsorbed on an immunologically-active adsorbent in a column and separated from the other proteins, the antibodies again eluted from the column and the Fab fractions split with papain and purified wherein the improvement comprises absorbing the digitalis antibodies on an immunologically-active absorbent which comprises an inorganic matrix to which digitoxin aldehyde is bound via a spacer which cannot be split with papain, treating the matrix with papain so as to split the absorbed antibodies into Fab and Fc fragments, washing the column so as to remove the Fc fragments, washing the column so as to remove the Fc fragments and excess papain, and desorbing the Fab fragments bound to the matrix with a suitable eluting agent.

2. Process according to claim 1, wherein porous glass is used as the inorganic matrix material.

3. Process according to claim 1, wherein triethoxysilylpropylamine is used as the spacer.

4. Process according to claim 1, wherein digitoxin aldehyde, obtained by the oxidation of digitoxin with periodate, is bound to the matrix as Schiffs base and the Schiffs base is reduced with sodium borohydride.

5. Process according to claim 1, wherein digoxin-glutaryl-O-hydroxysuccinimide bound to albumin is used as the agent for the immunizing.

6. Process according to claim 1, wherein the antibody containing globulin fraction is obtained by ammonium sulfate precipitation from the animal serum.

7. Process according to claim 1, wherein the aborption of the antibodies and the the removal of the Fc fragments and excess papain is effected with a phosphate/sodium chloride solution buffered to pH 7.

8. Process according to claim 1, wherein the Fab fragments desorbed from the column are further purified by chromatography on gels and/or ion exchangers.

9. Process according to claim 1 wherein the matrix is porous glass and the digitoxin aldehyde is bound thereto by triethoxysilylpropylamine as the spacer.

* * * * *